(12) United States Patent
Fan

(10) Patent No.: US 11,759,119 B2
(45) Date of Patent: *Sep. 19, 2023

(54) SURGICAL POSITIONING CIRCUIT

(71) Applicant: GYRUS ACMI, INC., Westborough, MA (US)

(72) Inventor: Tailin Fan, Nashua, NH (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/664,523

(22) Filed: May 23, 2022

(65) Prior Publication Data

US 2022/0280058 A1 Sep. 8, 2022

Related U.S. Application Data

(60) Continuation of application No. 15/652,580, filed on Jul. 18, 2017, now Pat. No. 11,369,281, which is a division of application No. 14/153,546, filed on Jan. 13, 2014, now Pat. No. 9,737,232.

(60) Provisional application No. 61/783,607, filed on Mar. 14, 2013.

(51) Int. Cl.
*A61B 5/00* (2006.01)
*A61B 5/05* (2021.01)
(Continued)

(52) U.S. Cl.
CPC ............... *A61B 5/05* (2013.01); *A61B 5/062* (2013.01); *A61B 5/6848* (2013.01);
(Continued)

(58) Field of Classification Search
CPC ........ A61B 2034/2051; A61B 17/3403; A61B 5/062
See application file for complete search history.

(56) References Cited

U.S. PATENT DOCUMENTS 4,136,360 A * 1/1979 Hoffrichter ............... H04N 1/60
358/523
4,426,874 A 1/1984 Moore
(Continued)

FOREIGN PATENT DOCUMENTS

CN 105338895 A 2/2016
CN 105338895 B 10/2020
(Continued)

OTHER PUBLICATIONS

"U.S. Appl. No. 14/153,546, Final Office Action dated Dec. 2, 2016", 9 pgs.
(Continued)

*Primary Examiner* — Rajeev P Siripurapu
(74) *Attorney, Agent, or Firm* — Schwegman Lundberg & Woessner, P.A.

(57) ABSTRACT

A surgical locator circuit identifies a surgical target such as a kidney stone by disposing an emitter such as a magnetic source behind or adjacent the surgical target, and employing the circuit to identify an axis to the emitter, thus defining an axis or path to the surgical target. An array of sensors arranged in an equidistant, coplanar arrangement each senses a signal indicative of a distance to the emitter. A magneto resistor sensor generates a variable resistance is responsive to the distance to a magnetic coil emitting a magnetic field. An equal signal from each of the coplanar sensors indicates positioning on an axis passing through a point central to the sensors and orthogonal to the plane. A fixed element and signal conditioner augments and normalizes the signal received from each of the sensors to accommodate subtle differences in magneto resistive response among the plurality of sensors.

16 Claims, 4 Drawing Sheets

(51) Int. Cl.
*A61B 17/34* (2006.01)
*A61B 5/06* (2006.01)
*G01R 33/00* (2006.01)
*G01R 33/09* (2006.01)
*A61B 34/20* (2016.01)
*A61B 5/20* (2006.01)
*A61B 90/00* (2016.01)

(52) U.S. Cl.
CPC ...... *A61B 17/3403* (2013.01); *G01R 33/0017* (2013.01); *G01R 33/0029* (2013.01); *G01R 33/09* (2013.01); *A61B 5/201* (2013.01); *A61B 2034/2051* (2016.02); *A61B 2090/3954* (2016.02); *A61B 2560/0223* (2013.01); *A61B 2562/04* (2013.01)

(56) References Cited

U.S. PATENT DOCUMENTS

| | | | |
|---|---|---|---|
| 4,930,347 | A | 6/1990 | Henderson |
| 5,309,136 | A | 5/1994 | Rezgui et al. |
| 6,301,775 | B1 | 10/2001 | Piazza |
| 6,888,346 | B2 | 5/2005 | Wincheski et al. |
| 7,009,268 | B2 | 3/2006 | Yang et al. |
| 9,737,232 | B2 | 8/2017 | Fan |
| 2002/0073869 | A1 | 6/2002 | Tiernan et al. |
| 2004/0011365 | A1 | 1/2004 | Govari et al. |
| 2005/0075562 | A1 | 4/2005 | Szakelyhidi, Jr. et al. |
| 2005/0200352 | A1 | 9/2005 | Haga et al. |
| 2005/0239230 | A1 | 10/2005 | Yang et al. |
| 2006/0061354 | A1 | 3/2006 | Wallance et al. |
| 2007/0167741 | A1 | 7/2007 | Sherman et al. |
| 2008/0074224 | A1 | 3/2008 | Castano et al. |
| 2009/0063081 | A1 | 3/2009 | Xu |
| 2010/0094116 | A1 | 4/2010 | Silverstein |
| 2011/0025318 | A1 | 2/2011 | Saruki et al. |
| 2011/0074406 | A1 | 3/2011 | Mather et al. |
| 2011/0169488 | A1 | 7/2011 | Mather |
| 2012/0166122 | A1 | 6/2012 | Bottinelli et al. |
| 2014/0275956 | A1 | 9/2014 | Fan |
| 2017/0167741 | A1 | 6/2017 | Otsuki et al. |
| 2017/0311838 | A1 | 11/2017 | Fan |

FOREIGN PATENT DOCUMENTS

| | | |
|---|---|---|
| EP | 1399749 A2 | 3/2004 |
| EP | 1467218 A2 | 10/2004 |
| EP | 2284555 A1 | 2/2011 |
| EP | 2562556 A2 | 2/2013 |
| EP | 2967411 A1 | 1/2016 |
| EP | 2967411 B1 | 3/2021 |
| JP | H0875835 A | 3/1996 |
| JP | 2002529133 A | 9/2002 |
| JP | 2004130094 A | 4/2004 |
| JP | 2006503621 A | 2/2006 |
| JP | 2007215993 A | 8/2007 |
| JP | 2010078401 A | 4/2010 |
| JP | 2010078404 A | 4/2010 |
| JP | 2011027683 A | 2/2011 |
| JP | 2013506141 A | 2/2013 |
| JP | 2016512457 A | 4/2016 |
| JP | 6251379 B2 | 12/2017 |
| WO | WO-2004034914 A2 | 4/2004 |

OTHER PUBLICATIONS

"U.S. Appl. No. 14/153,546, Non Final Office Action dated Jul. 7, 2016", 10 pgs.
"U.S. Appl. No. 14/153,546, Notice of Allowance dated Apr. 18, 2017", 5 pgs.
"U.S. Appl. No. 14/153,546, Preliminary Amendment filed May 18, 2016", 6 pgs.
"U.S. Appl. No. 14/153,546, Response filed Mar. 31, 2017 to Final Office Action dated Dec. 2, 2016", 6 pgs.
"U.S. Appl. No. 14/153,546, Response filed Nov. 7, 2016 to Non Final Office Action dated Jul. 7, 2016", 11 pgs.
"U.S. Appl. No. 15/652,580, Examiner Interview Summary dated Jan. 25, 2022", 3 pgs.
"U.S. Appl. No. 15/652,580, Final Office Action dated Aug. 4, 2020", 16 pgs.
"U.S. Appl. No. 15/652,580, Final Office Action dated Sep. 20, 2021", 14 pgs.
"U.S. Appl. No. 15/652,580, Non Final Office Action dated Feb. 24, 2020", 15 pgs.
"U.S. Appl. No. 15/652,580, Non Final Office Action dated Mar. 26, 2021", 15 pgs.
"U.S. Appl. No. 15/652,580, Notice of Allowance dated Feb. 24, 2022", 7 pgs.
"U.S. Appl. No. 15/652,580, Response filed May 26, 2020 to Non Final Office Action dated Feb. 24, 2020", 11 pgs.
"U.S. Appl. No. 15/652,580, Response filed Jun. 28, 2021 to Non Final Office Action dated Mar. 26, 2021", 13 pgs.
"U.S. Appl. No. 15/652,580, Response filed Jan. 20, 2022 to Final Office Action dated Sep. 20, 2021", 13 pgs.
"U.S. Appl. No. 15/652,580, Response filed Nov. 4, 2020 to Final Office Action dated Aug. 4, 2020", 11 pgs.
"Chinese Application Serial No. 201480014483.9, Office Action dated Mar. 1, 2019", with English translation, 16 pgs.
"Chinese Application Serial No. 201480014483.9, Office Action dated Dec. 3, 2019", with English translation, 10 pgs.
"Chinese Application Serial No. 201480014483.9, Response filed Apr. 17, 2020 to Office Action dated Dec. 3, 2019", w/ English Claims, 10 pgs.
"Chinese Application Serial No. 201480014483.9, Response to Examiners Telephone Interview filed Jun. 18, 2020", w/ English Claims, 10 pgs.
"European Application Serial No. 14764681.4, Communication Pursuant to Article 94(3) EPC Sep. 6, 2017", 7 pgs.
"European Application Serial No. 14764681.4, Extended European Search Report dated Mar. 11, 2016", 8 pgs.
"European Application Serial No. 14764681.4, Response filed Apr. 16, 2020 to Summons to Attend Oral Proceedings mailed Jan. 27, 2020", 37 pgs.
"European Application Serial No. 14764681.4, Response filed Sep. 26, 2016 to Extended European Search Report dated Mar. 11, 2016", 8 pgs.
"European Application Serial No. 14764681.4, Response filed Dec. 28, 2017 to Communication Pursuant to Article 94(3) EPC dated Sep. 6, 2017", 46 pgs.
"European Application Serial No. 14764681.4, Summons to Attend Oral Proceedings mailed Jan. 27, 2020", 8 pgs.
"International Application Serial No. PCT/US2014/011238, International Search Report dated Apr. 25, 2014", 3 pgs.
"Olympus ScopeGuide Receives FDA Clearance", Center Valley, PA, <http://www.olympusamerica.com/oai_pressDetails.asp?pressNo=851>, (May 24, 2011), 2 pgs.
Li-Ming, Su MD, et al., "Robotic Percutaneous Access to the Kidney: Comparison with Standard Manual Access", J. Endourology, 16:7, (2002), p. 471.
Robert, Marcovich, et al., "Percutaneous Renal Access: Tips and Tricks", BJU International, (2005), p. 78.
U.S. Appl. No. 14/153,546 U.S. Pat. No. 9,737,232, filed Jan. 13, 2014, Surgical Positioning Circuit.
U.S. Appl. No. 15/652,580 U.S. Pat. No. 11,369,281, filed Jul. 18, 2017, Surgical Positioning Circuit.

\* cited by examiner

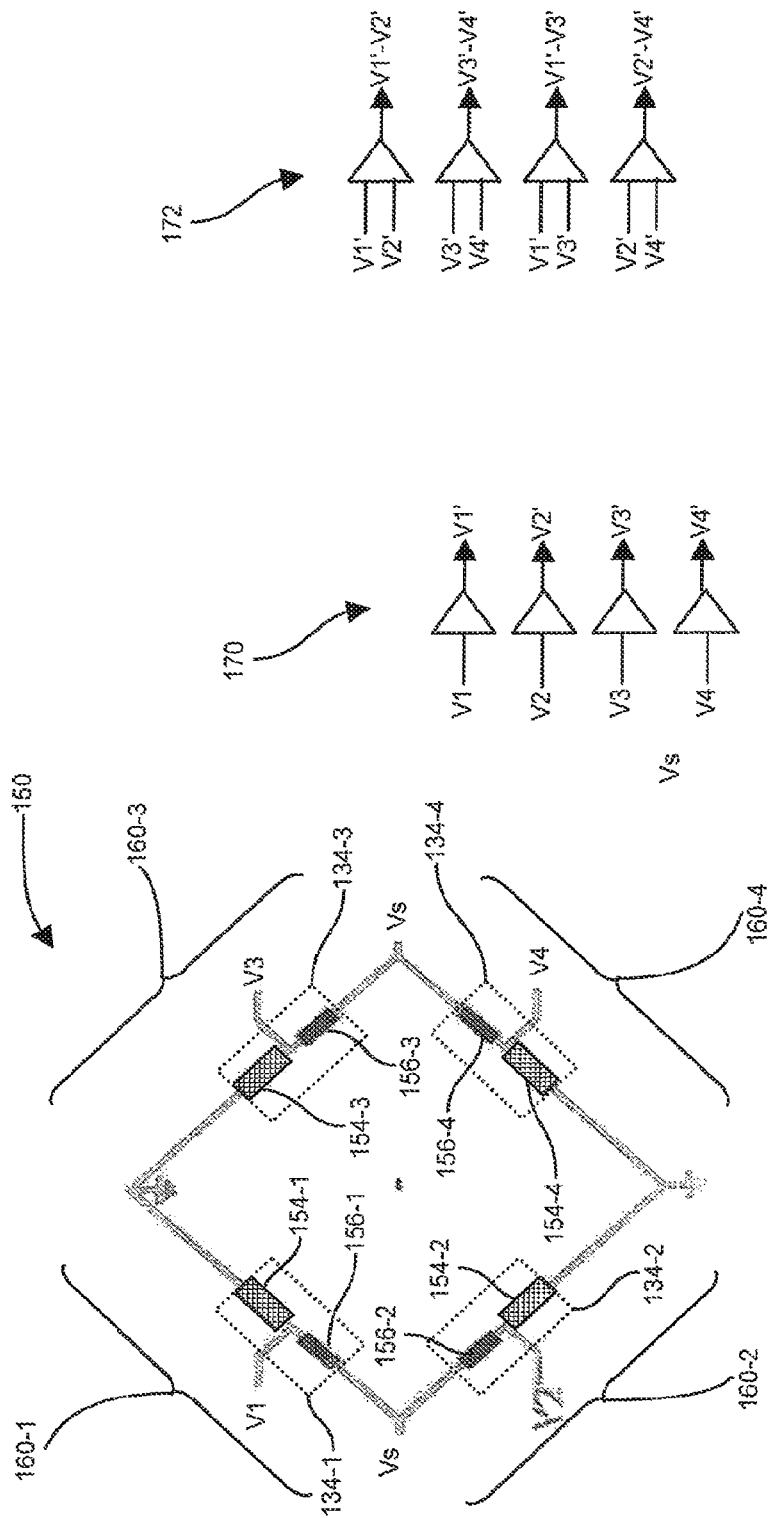

SURGICAL POSITIONING CIRCUIT

RELATED APPLICATIONS

This application is a Continuation of U.S. patent application Ser. No. 15/652,580 filed Jul. 18, 2017, which is a divisional of prior U.S. patent application Ser. No. 14/153,546 filed Jan. 13, 2014 entitled SURGICAL POSITIONING CIRCUIT, now issued as U.S. Pat. No. 9,737,232, which claims benefit of the priority of U.S. Provisional Patent Application Ser. No. 61/783,607 filed Mar. 14, 2013, the entire teachings of which are incorporated herein by this reference.

BACKGROUND

Surgical procedures often rely on precise positioning to locate particular surgical targets without disturbing nearby structures that may adversely affect the surgical results. Open field surgery relies on a steady hand and sharp eye of a surgeon for ensuring that surgical intervention is focused accordingly. In recent decades, endoscopic and laparoscopic techniques perform minimally invasive procedures with elongated instruments by working through small incisions, rather than a large open field. Many procedures involve simply locating and removing a harmful growth or structure, such as a tumor, cyst or polyp. In the case of kidney stones, for example, the stone may be broken up and removed, once located with endoscopic equipment.

SUMMARY

A surgical locator circuit identifies a surgical target such as a kidney stone by disposing an emitter such as a magnetic source behind or adjacent to the surgical target, and employing the circuit to identify an axis to the emitter, thus defining an axis or path to the surgical target. An array of sensors arranged in an equidistant, coplanar arrangement senses a signal indicative of a distance and direction to the emitter. In the case of a magneto resistor sensor, a variable resistance is responsive to the distance and direction from the magneto resistor to an emitter defined by a magnetic coil emitting a magnetic field. An equal signal from each of the coplanar sensors indicates positioning on an axis passing through a point central to the sensors and orthogonal to the plane. A fixed element and signal conditioner augments and normalizes the signal received from each of the sensors to accommodate subtle differences in magneto resistive response among the plurality of sensors.

Configurations herein are based, in part, on the observation that surgical locator and placement devices rely on precise positioning and corresponding electronic circuitry that can discriminate between minute electrical signals to effectively relay positioning information. Unfortunately, conventional approaches suffer from the shortcoming that individual electronic components may have a subtle variation in physical characteristics, leading to a corresponding variation in signal or stimuli response, even for supposedly identical or equivalent components having the same design specifications. These subtle variations, while insignificant in many applications and perhaps within the published tolerances of the component, may still produce an undesirable variation in a surgical positioning device. Accordingly, configurations herein disclose a fixed element in conjunction with a sensing element for normalizing a sensor signal received from a plurality of sensing elements. The fixed element provides a known response or signal, which allows a signal conditioner to adjust the sensor signal from each of the plurality of sensors such that each sensor generates a calibrated, consistent signal that offsets any variance in the individual sensor signals. Therefore, a consistent response, and thus consistent positioning information, is received from all the sensors in the sensor array.

In an example arrangement as discussed below, the sensor element is a magneto resistor that varies resistance in response to a magnetic field, and the fixed element a fixed resistor that maintains a constant resistance. The combined magneto resistor and fixed resistor each define one leg of four legs in a modified wheatstone bridge configuration. A wheatstone bridge, as is known in the art, has four legs in a square arrangement, and is connected to a voltage source such that the ratio of the resistance of two of the legs is equivalent to the ratio of resistance of the other two legs. Configurations herein allow for determining a distance and direction from an axis passing through the middle of the square, hence being equidistant from each of the legs (assuming the sensor elements define similar positions around the square). In implementation, the resistive values of the magneto resistor are equal when aligned on a central axis normal to a plane defined by the magneto resistors (sensors). Hence an output signal defined by the difference of the voltage across each of the legs will be zero.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4C show a sensor array circuit of the positioning device.

DETAILED DESCRIPTION

The following examples and discussion illustrate various configurations of the disclosed approach. In the example configuration, the proposed approach facilitates the alignment of a percutaneous nephrolithotomy needle with the targeted calyx. Such alignment is a precise step during percutaneous nephrostomy, which prepares for a percutaneous nephrolithotomy (PCNL) procedure, more commonly referred to as a kidney stone removal. During such a procedure, the task of obtaining access manually requires substantial skill and can be particularly difficult when the collecting system is not dilated. Inaccurate placement of the needle can risk injuring the kidney and adjacent organs, thus compromising the planned percutaneous procedure, as well as the clinical outcome of the patient.

Figure 1:
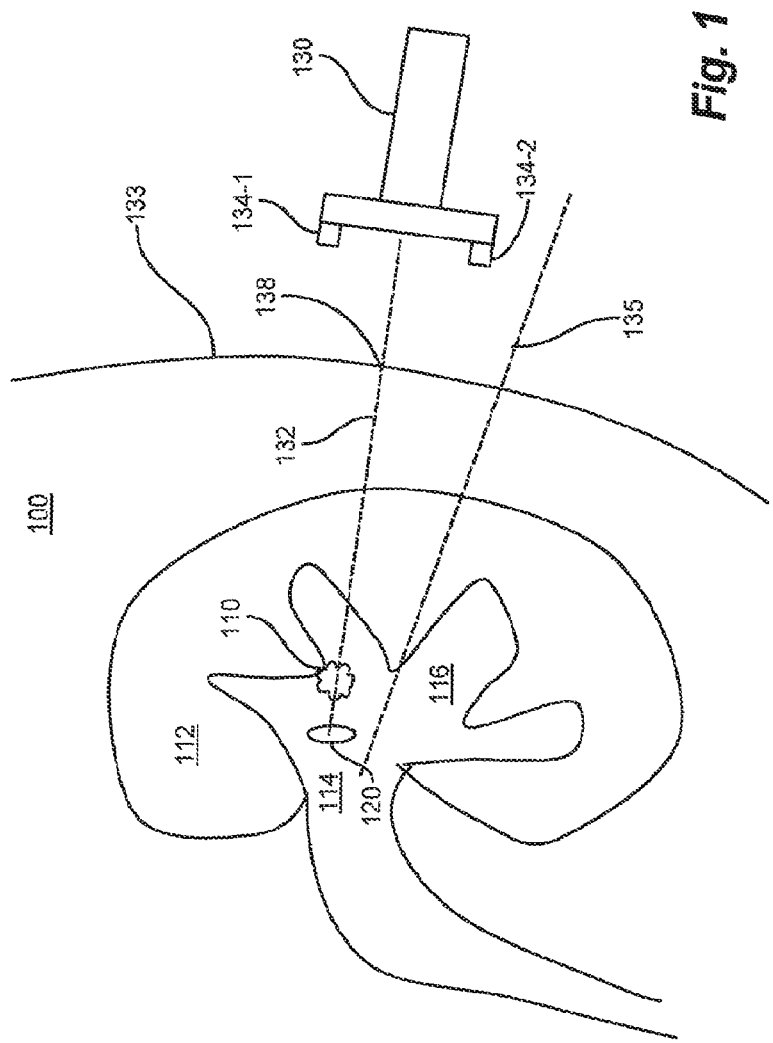
FIG. 1 shows a context view of a positioning device as disclosed herein.

FIG. 1 shows a context view of a positioning device 130 as disclosed herein. Referring to FIG. 1, in a particular example, a patient 100 undergoes a procedure for removal of a surgical target 110 such as a kidney stone from a kidney 112. A signal source 120 such as a magnetic coil is surgically disposed on a distal side 114 of the kidney stone 110. The signal source 120 may be disposed by any suitable method, typically by endoscopic instruments into a void 116 of the kidney 112. The positioning device 130 is disposed externally on or near the surgical surface 133 (i.e. skin) of the patient 100. The positioning device 130 locates an axis 132 to the signal source, by comparing distance and relative orientations from each of a plurality of sensors 134-1, 134-2 (134 generally) to the signal source 120. It should be noted that the sensors 134 detect a magnetic field strength, which is related to the distance although based on the field orientation as well. Thus, the orientation of the sensors 134 seeks to locate the axis 132 by field strength indicative of orientation and distance from the signal source 120. By positioning the signal source 120 on the axis 132 and behind the kidney stone or other surgical target 110, the positioning device 130 locates an insertion point 136 and angle on the axis 132 which can then be followed to reach the surgical target 110. The positioning device 130 therefore ensures surgical insertion on the axis 132 for intersecting with the surgical target 110, improving upon conventional approaches which have the potential for inadvertent needle insertion along an incorrect path. Therefore, alignment on the axis 132 is facilitated by unbalanced sensor readings resulting from alignment along axes offset from 132, for example 135, as discussed further below. In one embodiment, the device of the present invention may work with a signal source 120 located at the distal tip of an endoscope. The endoscope allows for direct observation of the target and placement of the signal source directly behind the target stone.

Figure 2:
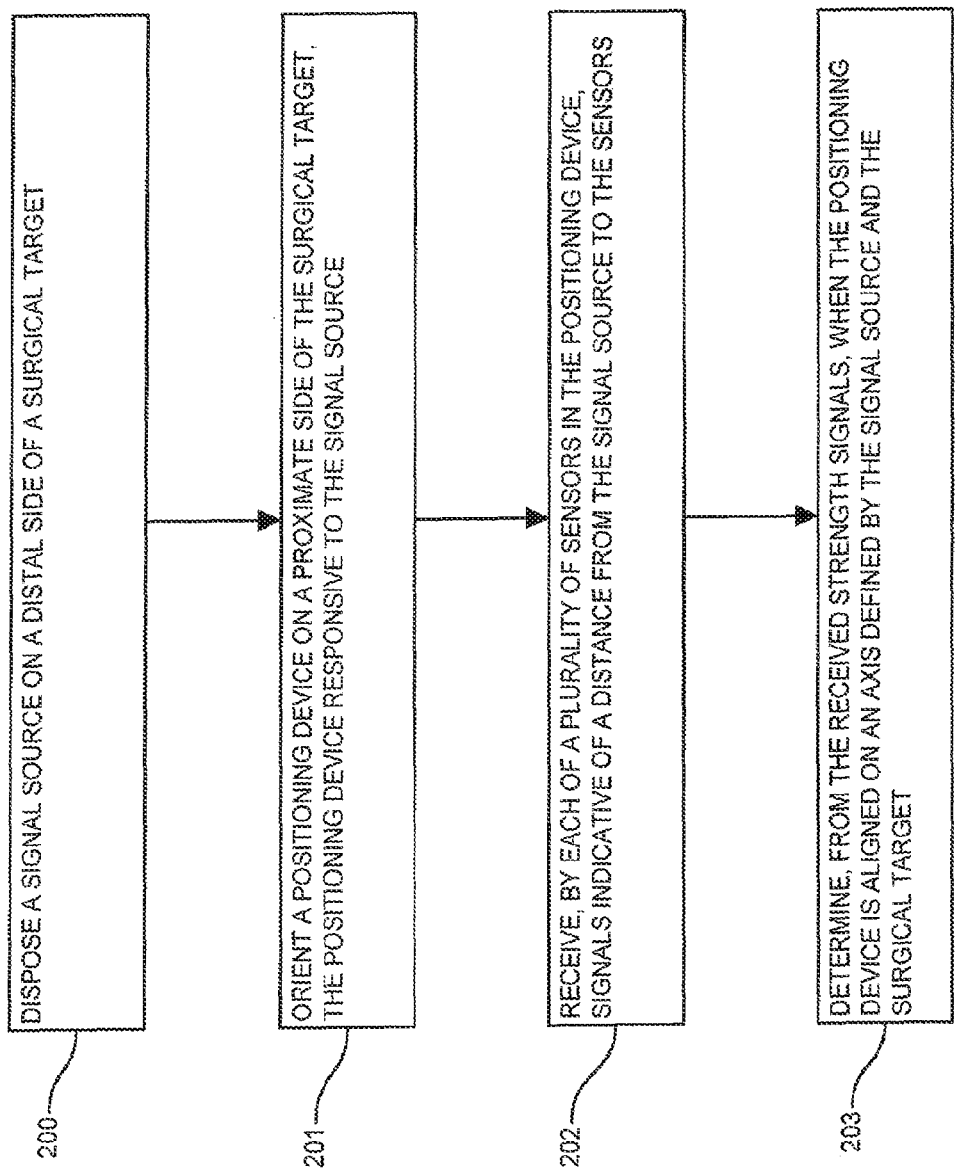
FIG. 2 shows a flowchart of locating a surgical target using the positioning device of FIG. 1.

FIG. 2 shows a flowchart of locating a surgical target using the positioning device of FIG. 1. Referring to FIGS. 1 and 2, the method of sensing a surgical target as disclosed and shown herein includes disposing a signal source 120 on a distal side 114 of a surgical target 110, as depicted at step 200. The surgeon or other operator orients the positioning device 130 on a proximate side of the surgical target 110, such that the positioning device 130 is responsive to the signal source 120, as shown at step 201. A sensor circuit in the positioning device 130 receives, by each of a plurality of sensors 134 in the positioning device 130, signals indicative of a distance and orientation from the signal source 120 to the sensors 134, as depicted at step 202. The sensor circuit (shown in greater detail as 150, below) defines a positioning system, discussed in more detail below, for determining, from the received strength signals, when the positioning device 130 is aligned on an axis 132 defined by the signal source 120 and the surgical target 110, as disclosed at step 203. In the example arrangement, the signal source 120 is a magnetic coil and the sensors 134 include a magneto resistor responsive to a magnetic field indicative of the distance from the magnetic coil to the sensor 134.

In a general implementation, the positioning system consists of an internal target such as the kidney stone 110, an external target, defined by the signal source 120, attached to a surgical needle, a detection system including a sensor circuit 150 for localizing the coordinates of these in 3-D space around the patient, and a display system for the user. The internal target is a single energy source that is detected and localized in 3-D space by the detection system. The target needle has two or more similar energy sources located along its length. Each of these sources are detected and localized in 3-D space by the detection system. The spatial location information from the detection system for the multiple sources on the needle generates a vector in 3-D space while the spatial location information for the internal target generates a point in 3-D space. This information is sent to the user interface display system.

The positioning system updates continuously, enabling the surgeon or user to visualize the location and orientation of the vector relative to the point. This continuous stream of information provided to the user by the system enables the needle to be directed and steered towards the internal target in real time. The surgical needle may employ any suitable technique for inserting and positioning the signal source 120 on axis 132 with the surgical target 110.

The disclosed positioning system for detection and spatial location of any of the targets could be achieved through a variety of physical detection mediums. Any of the aforementioned sources could be a single point emitter. This generally employs electrical or acoustic energy source which could be but is not limited to magnetic, ultrasound, high frequency RF energy, low frequency RF energy, time varying magnetic fields, or time varying electrical fields. The positioning system could comprise a plurality of appropriate, non co-located energy sensors located outside the body. Each sensor would utilize some detection scheme to determine the linear distance between it and the emitting energy source. This could be accomplished by detection using an appropriate energy receiver and multiple means including but not limited to: 1) utilizing phase information of the signal driving the source as the phase varies with the time of flight, and 2) measuring the change in the amplitude of the received energy as it varies with distance between the emitter and receiver, or 3) utilizing the trip time of flight of a change in signal amplitude such as a chirp or pulse. Other measuring schemes for determining the distance between the sensor and emitter based on advance phased-array detection may also be envisioned.

In operation, distance information from each of the plurality of sensors 134 in the detector system is used to localize a given signal source 120 in 3-D space. In the example approach this is accomplished by arranging the detectors into an array with know spatial locations and employing triangulation with the measured distances. More advanced methods are possible, for example using phased-array schemes such as phased array antenna or synthetic aperture antenna methods.

In the example configuration of the PCNL Target Finding system (PCNL TF) includes two major subsystems, an Internal Target Object (ITO) (defined by the signal source 120) and an External Target Finder (ETF), defined by the positioning device 130. The ITO is a magnetic field generating device that is deployed through the working channel of a flexible ureteroscope, or as a built-in part inside the tip of the ureterosocope. At the tip of the ITO is a small head that produces a magnetic field, static or pulsed. Under visual guidance through the ureteroscope, the tip of the ureteroscope is positioned in front of the stone infected calyx, and so is the tip of the ITO, positioned/oriented facing the stone in the calyx. The ETF is a hand-held or robot/mechanical arm mounted magnetic field sensing device. It is instrumented such that when the center of this device is aligned with the magnetic field produced by the ITO, it will signal such alignment is established. A center guidance channel then can guide the access needle towards the calyx in the kidney inside the body. The entire system works based on the fact that human body is largely "transparent" to static magnetic fields and the magnetic part of low frequency electromagnetic wave, in contrast with conventional x-ray or ultrasound approaches which encounter difficulty in distinguishing soft tissue structures. In this configuration, the ITO's magnetic field generating component is isolated and represented by a coil defining the signal source 120, with all other parts on the ITO and the ureterosocope omitted for clarity. The various body tissues separating the ITO and ETF is combined and represented as one barrier as surgical surface 133, now described in operation in greater detail.

Figure 3:
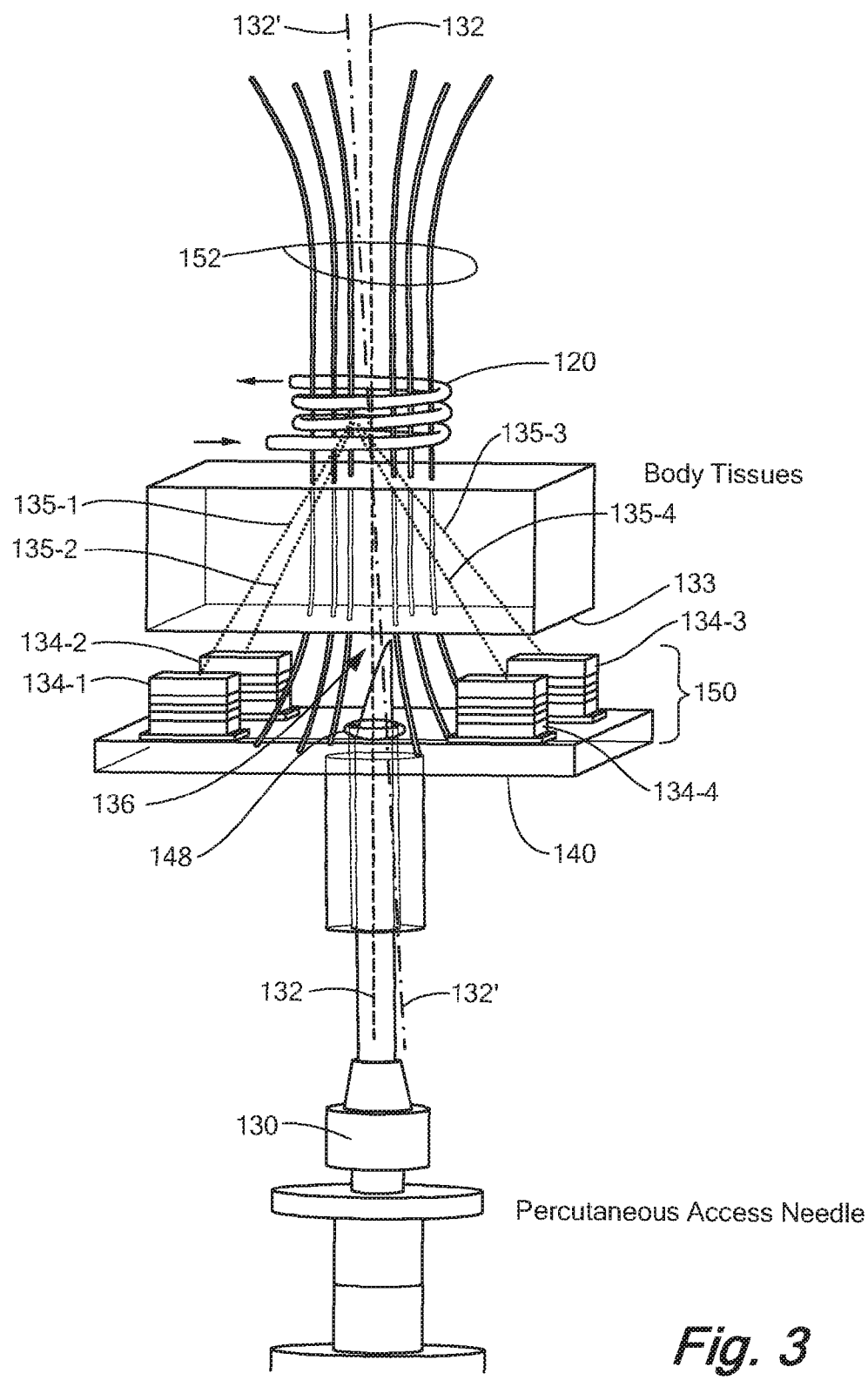
FIG. 3 is a diagram of the positioning device of FIG. 1 in operation.

FIG. 3 is a diagram of the positioning device of FIG. 1 in operation. Referring to FIGS. 1 and 3, a generalized positioning device suitable for use with configurations herein is disclosed. In FIG. 3, the positioning device 130 employs four sensors 131-1 . . . 134-4, arranged in a square, arrangement on a planar base 140 of the positioning device 130 to define a sensor circuit 150 defining an array of sensors 134 (sensor array circuit). The use of a planar base 140 and equidistant square arrangement provides for a uniform signal when the sensors are disposed orthogonally centered on the axis 132 passing through the center 148 of the planar base 140. In the example configuration, the signal source 120 is a magnetic coil and the sensors 134 are magneto-resistors that vary resistance in response to a magnetic field 152 emitted by the signal source 120. The distance from the sensors 134-1 . . . 134-4 is shown by dotted lines 135-1 . . . 135-4, respectively. When the distances 135-1 . . . 135-4 are equal, the response (i.e. resistance) of each of the sensors 134 is equal.

FIGS. 4A-4C show a sensor array circuit 150 of the positioning device. Referring to FIGS. 3 and 4A, each sensor 134 includes a variable element 154 and a fixed element 156, labeled 154-1 . . . 154-4 and 156-1 . . . 156-4, as per their sensor 134 counterparts. In the example arrangement, the variable elements 154 are magneto-resistors which vary a resistance in response to magnetic field strength from the magnetic source 120, and the fixed elements 156 are resistors having a known value. The sensor array circuit 150, therefore includes four legs 160-1 . . . 160-4 (160 generally), each leg 160 having a sensor 134 including a variable element 154 and a fixed element 156. Each leg also has a voltage value V1 . . . V4 is taken from the leg 160 between the fixed 156 (shown as solid) and variable elements 154 (shown as crosshatched). A source voltage Vs provides a known voltage to each leg 160, and connects to the fixed element 156 side of each leg, while the variable elements 154 connect to ground for providing a voltage drop V1 . . . V4 value, discussed further below.

Each of the variable elements 154, or magneto-resistors, has a rest value (resistance) representing zero field strength. In the configuration disclosed herein, the positioning device 130 relies upon minute changes in the signal received from each of the sensors 134. Each of the variable elements 154 may have a slightly different rest value, depending on subtle variations in manufacturing that are infeasible to eliminate. Accordingly, response to the magnetic field 152 for each of the variable elements 154 may be slightly different. Upon application of the source voltage Vs, a corresponding current 11 . . . 14 flows in each leg 160. Since the current in each leg 160 is the same across both the fixed and resistive element, the voltage V1 . . . V4 across variable elements 154 can be used to determine the corresponding field strength at the location of each variable element 154. By calibrating against a rest or known magnetic field, a conditioning value is computed for each V1 . . . V4 to complement the resistive value of the variable element 154. The current through the leg 160 varies in response to resistance changes in variable element 154, in response to changes in magnetic field strength. Vs is constant and V1 . . . 4=Vs*R(154)/R(156). Thus, V1 . . . 4 is proportional to variable element 154.

Thus, when Vs connects to the sensor array circuit 150, each magneto-resistor (variable element) 154 has a particular RO, corresponding to its value at zero field strength. On each leg, the fixed resistive value (value of the fixed element 156) corresponds to the value of the variable element 154 on the same leg 160, and the two element (resistors) 154, 156 form a voltage divider. The voltages V1 . . . V4 reflect the voltage drop across the variable elements 154, which represents the field strength at that location in the sensor array circuit 150.

Referring to FIGS. 4B and 4C, the voltages V1 . . . V4 across the four variable sensors 154 are conditioned in step 170, which may include amplification, buffering, and other transformations) to generate V1' . . . V4'. The voltage across 134 is constant, Vs. The gain in step 170 used for each sensor 134 output is calibrated such that when the field 152 strength is the same, i.e. centered and orthogonal on the axis 132 in the example shown, the conditioned values of V1' . . . V4' are also the same or substantially equivalent.

A multi channel voltage comparator 172 then uses these voltages V1' . . . V4' as inputs, outputs their difference for computing when the positioning device 130 is on the axis 132 and aimed toward the target 110 (FIG. 1). It should be noted that the plurality of sensors 134, shown in the example as 134-1 . . . 134-4 although other numbers of sensors could be employed, may be calibrated individually, thus the difference of physical parameters and response between the magneto resistors (variable elements 154) is accommodated.

The disclosed positioning device 130 therefore includes a sensor circuit for identifying a surgical target having various features that are discussed further below as components of or steps performable by the various configurations. The positioning device 130 includes a plurality of sensors 134 arranged in a plane substantially orthogonal to an axis 132 passing through the surgical target 110, such that the axis is defined by an emitter or signal source 120 disposed on a distal side 114 of the surgical target 110. Target 120 can be a permanent magnet, a current-carrying coil, or the like, or any combination thereof. In one embodiment, target 120 is a signal source disposed at the end of an endoscope and is of a compact size to make such a disposition possible. The method of sensing a surgical target therefore includes disposing the signal source 120 on a distal side of the surgical target 110, and orienting the positioning device 130 on a proximate side of the surgical target, in which the positioning device 130 is responsive to the signal source 120.

The sensor circuit 150 includes a plurality of circuit legs 160 interconnecting the plurality of sensors 134, such that each sensor is disposed on a respective circuit leg 160. A voltage source connects to each of the circuit legs 160 for inducing an output signal, partly depending on the orientation of the plurality of sensors 134 relative to the axis 132, such that the output signals from each leg 160 are of equal or substantially equivalent value when the plane of base 140 is orthogonal to the axis 132 and the axis is substantially centered between the sensors 134. The output value may vary, depending on the distance and orientation of base 140 from source 120. Locating the axis 132 includes receiving, by each of a plurality of sensors 134 in the positioning device 130, signals indicative of the distance 135 and orientation from the signal source 110 to the sensors 134, and determining, from the received signal strengths, when the positioning device is aligned on the axis 132 defined by the signal source. Orientation on another axis 135 that is not centered and aligned with the target will yield unbalanced values in at least one of the sensors 154, due to variances in field strength. In operation, varying the position of the device 130 allows an operator to "home in" from the unaligned axis 135 until aligned on the axis 132

A calibration adjusts each of the strength signals to accommodate a variance between the strength of the signals received by each of the sensors 134, due to small variances between the signals (resistance) given by the magneto resistors even when disposed at the same distance and orientation. The sensor circuit 150 disposes a fixed resistor 156 adjacent to each of the sensors (magneto resistors) 154 on the respective circuit leg 160. Variable gain adjustment may be accomplished in step 170 of FIG. 4B. Appropriate gain may be determined in the absence of magnetic field signal, in the presence of a known calibrating magnetic field with its axis fully aligned to sensor board axis 132', or both, to correct for small inconsistencies in the fixed resistor values and determine appropriate gain values to calibrate outputs V1 . . . V4. Then, in the presence of a magnetic field during an active procedure, signal output V1 . . . V4 is again run through gain step 170 to get an accurate reading of magnetic field direction and orientation from the sensor circuit 150. A comparator may be used, as in FIG. 4C, for comparing a known signal strength reading from the fixed element (resistor) 156. Fixed resistor 156 has a predictable voltage drop, such that adjusting further includes computing the predictable voltage drop across the fixed resistor, and conditioning the signal received from each of the plurality of sensors such that the conditioned signal is equivalent for each of the sensors 154 at a rest position of the aligned positioning device. Thus, the fixed resistor 156 is responsive to the signal from the voltage source and has a constant resistance regardless of orientation or distance, in contrast to the magneto resistor that varies with the strength and orientation of the magnetic field 120.

In other words, the sensor circuit 150 defines its own central axis 132' following calibration by the signals V1'-V4'. Alignment of the sensor circuit 150, and therefore of the device 130, occurs when the sensor circuit axis 132' aligns with the target axis 132, indicating that the sensor circuit 150, and therefore the positioning device 130, is directed toward the surgical target 110 defined by the magnetic source 120. Therefore, if when the sensors are disposed equally distanced/oriented towards the magnetic source 120, and aligned on axis 132, the output from a sensor differs from others, then calibration is to amplify individual output V1' . . . V4' accordingly so that the outputs are equal when an axis of the circuit 132' is aligned with the axis 132 indicating the desired insertion 132, as in FIG. 4B.

It is contemplated that the circuit of the present invention could be used for some other kind of calibration. For example, the sensed field may be light, radiation, or other range of the electromagnetic spectrum, and the sensor 134 may be one that is suitable to the type of field sensed. The teachings of the present invention are such that circuit 150 has a fixed resistor 156 for each variable resistor 154 as this provides an effective way of getting the varied resistance value of variable resistor 154 read out as a voltage. Variable resistor 154 and fixed resistor 156 in series form a voltage divider to divide Vs according to the ratio between variable resistor 154 and fixed resistor 156 In the example configuration, the sensors 134 define a plane and the signal strengths indicate when the defined plane is orthogonal to the axis 132. The sensors 134 are in equidistant orientation on circuit legs, typically in a square arrangement, and centered about the central axis 132' such that the received signals from each of the sensors is equal when the plane of the sensor circuit 150 aligns orthogonal to the axis 132 and centered between the sensors 134. In the process of targeting, the disclosed method attempts to align axis 132' with axis 132 from the signal source.

In the example arrangement, the emitter or signal source 120 is a magnetic source emitting a magnetic field 152, and the sensors 134 are magnetic sensors responsive to a strength and orientation of the emitted magnetic field. In this configuration, the variable element 154 is a magnetic field sensor having a variable resistance in response to the magnetic field 152 (also known as a magneto sensor) and the fixed element 156 is a static resistor having a linear response to the voltage source unaffected by the magnetic field 152. A calibration reference V1 . . . V4 taken between ground and the corresponding variable element (magneto resistor) 154 measures the strength of the magnetic field 152. Conditioning parameters provided by amplifiers 170 define V1' . . . V4', which are selected to offset the calibrated reference V1 . . . V4 such that equal values V1' . . . V4' are received when the circuit axis 132' is centered.

The conditioning parameters are utilized by a signal conditioner 170, such that the signal conditioner receives the calibration reference V from each of the circuit legs 160 and is responsive to the conditioning parameter for modifying the output signal for uniform response from each of the fixed resistors 156. The fixed element 156 is connected in series between the voltage source and the variable element 154, such that the calibration reference provides a signal indicative of a current flow based on the sensor, the current flow consistent through the sensor and the calibration reference and the signal indicative of a voltage drop across the calibration reference. A multi-channel comparator receives the modified output signal and matching the predetermined value based on the modified output signal.

Configurations herein include a sensor circuit operable for identifying a signal source in a variety of contexts in addition to the PCNL procedure as disclosed. The sensor circuit includes a plurality of legs 160 disposed in a coplanar arrangement, each leg of the plurality of legs having a sensor indicative of a distance to a magnetic source, and a voltage source connected to each of the legs. A fixed element 156 connected to each of the legs has a response to the voltage source independent of the magnetic source, and a calibration reference is defined by a terminal or contact between the fixed element and voltage source, such that the calibration reference is indicative of a voltage drop across the fixed element. In the example arrangement, the plurality of legs 160 and corresponding sensors define a modified wheatstone bridge, such that the calibration reference is responsive to a current flow in the respective leg and defines a voltage divider implemented as a half bridge of the wheatstone bridge arrangement.

The disclosed modified wheatstone bridge is such that the fixed element 156 is connected in series with each of the variable elements 156 (variable magnetic sensors) and has a common current level as the corresponding sensor element due to the series current flow. The signal conditioner has a conditioning parameter for each of the variable elements 156 for reading taken on the respective circuit leg, such that the conditioning parameter is for augmenting a signal received from the calibration reference such that augmented signal from each of the calibration references is the same when each of the sensors is the same distance from the magnetic source. The conditioning parameter thus allows computation of a consistent signal from each of the legs 160 when the plane defined by the legs is normal to an axis 132 centered between the sensors 134.

In an alternate arrangement, the external target and the detection system could be mechanically coupled to simplify the system overall. In this case the PCNL needle would be coupled through mechanical means directly or indirectly to the detection system. This eliminates some of the information necessary in determining the relative spatial locations of the internal target and the external targets defining the position of the PCNL needle. The location and orientation of the needle relative to the detection system would be predetermined. This information would then be used to simplify the solution of the equations involved in triangulation between the internal target and the external targets. This could be accomplished through a rigid mounting mechanism that would align the needle in a fixed orientation relative to the sensors in the detection system. The PCNL needle and detection assembly as a combined unit could then be steered in real time towards the internal target. In a less restricted implementation the mechanical coupling would allow one or more degrees of freedom between the PCNL needle and the detection system. This could be accomplished with an articulation mechanism and appropriate indexing sensors or using stepper motors or other similar methods. This information giving the relative location and orientation of the PCNL needle relative to the sensors in the detection system would then become part of the solution of the triangulation equation to locate these relative to the internal target.

Configurations disclosed herein include at least some features that may be implemented by a computer or similar processor based set of programmed instructions. Alternate configurations of the invention may therefore include a multiprogramming or multiprocessing computerized device such as a multiprocessor, controller or dedicated computing device in either a handheld, mobile, or desktop form or the like configured with software and/or circuitry (e.g., a processor as summarized above) to process any or all of the method operations disclosed herein as embodiments of the invention. Still other embodiments of the invention include software programs such as a Java Virtual Machine and/or an operating system that can operate alone or in conjunction with each other with a multiprocessing computerized device to perform the method embodiment steps and operations summarized above and disclosed in detail below. One such embodiment comprises a computer program product that has a non-transitory computer-readable storage medium including computer program logic encoded as instructions thereon that, when performed in a multiprocessing computerized device having a coupling of a memory and a processor, programs the processor to perform the operations disclosed herein as embodiments of the invention to carry out data access requests. Such arrangements of the invention are typically provided as software, code and/or other data (e.g., data structures) arranged or encoded on a computer readable medium such as an optical medium (e.g., CD-ROM), floppy or hard disk or other medium such as firmware or microcode in one or more ROM, RAM or PROM chips, field programmable gate arrays (FPGAs) or as an Application Specific Integrated Circuit (ASIC). The software or firmware or other such configurations can be installed onto the computerized device (e.g., during operating system execution or during environment installation) to cause the computerized device to perform the techniques explained herein as embodiments of the invention.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A positioning system to identify a surgical target in a human body, the positioning system comprising:
   a signal source configured to be disposed on a distal side of the surgical target, the signal source including a magnetic source; and
   a positioning device configured to be located on an external side of the human body, the positioning device including:
      a sensor circuit including:
         a plurality of sensors configured to be arranged in a plane orthogonal to an axis passing through the surgical target and the magnetic source, each sensor of the plurality of sensors including a variable element and a fixed element; and
         a voltage source configured to be connected to the fixed element, wherein the variable elements are configured to be connected to ground, the voltage source configured to induce an output signal related to an orientation of each sensor of the plurality of sensors relative to the axis;
      one or more processors; and
      a memory configured to store instructions executed by the one or more processors to perform the following:
         calculating a calibration reference of each sensor of the plurality of sensors between the fixed element and the voltage source, the calibration reference indicative of a voltage drop across the fixed element;
         augmenting a signal received from the calibration reference such that an augmented signal from each of the calibration references is the same when each of the sensors is the same distance from the magnetic source; and
         computing a calibrated signal that offsets any variance in the signal from each of the sensors of the plurality of sensors when the plane defined by the plurality of sensors is normal to an axis centered between the sensors;
      wherein the positioning device is configured to be aligned on the axis defined by a positioning axis passing through the magnetic source and the surgical target when the output signal from each of the sensors of the plurality of sensors are equivalent values.

2. The positioning system of claim 1, wherein each sensor of the plurality of sensors is disposed on a leg of the circuit.

3. The positioning system of claim 1, wherein each sensor of the plurality of sensors is disposed on a corresponding leg of a plurality of circuit legs.

4. The positioning system of claim 3, wherein the plurality of circuit legs interconnect the plurality of sensors.

5. The positioning system of claim 1, wherein the memory storing instructions are configured to be used to calculate a signal indicative of a field strength from the magnetic source at each sensor of the plurality of sensors.

6. The positioning system of claim 1, wherein the memory storing instructions includes instructions for:
   receiving an output signal from each of the sensors indicative of a field strength from the magnetic source at the plurality of sensors.

7. The positioning system of claim 1, wherein the magnetic source emits a magnetic field, and the sensors are magnetic sensors responsive to a strength and orientation of the emitted magnetic field.

8. The positioning system of claim 1, wherein the fixed element is a static resistor having a linear response to the voltage source unaffected by a magnetic field.

9. A positioning system to identify a surgical target in a human body, the positioning system comprising:

a signal source configured to be disposed on a distal side of the surgical target, the signal source including a magnetic source;

a positioning device configured to be disposed on a proximate side of the surgical target wherein the positioning device is responsive to the signal source; and a sensor circuit including:

a plurality of sensors coupled with the positioning device;

wherein each sensor of the plurality of sensors has a variable element and a fixed element, the fixed element having a response to a voltage source independent of the signal source, and the variable element having a variable resistance in response to a field strength of the magnetic source;

a multichannel voltage comparator receiving and comparing signals emitted from the signal source;

a plurality of calibration references wherein each calibration reference is taken between the variable element and the fixed element, the calibration reference indicative of a strength of a magnetic field, wherein the calibration reference is adjusted until the plurality of calibration references are equal in value;

one or more processors; and a memory storing instructions configured to store instructions executed by the one or more processors;

wherein the positioning device is configured to be aligned on an axis extending between the signal source and the surgical target when the multichannel voltage comparator compares signals output from the signal source that are equivalent in value.

10. The positioning system of claim 9, wherein a plurality of circuit legs interconnects the sensors, each sensor output strength signals indicative of a field strength from the signal source.

11. The positioning system of claim 10, wherein the strength signals are amplified to accommodate a variance of the strength of the signals received by each of the sensors.

12. The positioning system of claim 9, wherein each fixed element from the plurality of sensors has a specified value fixed element signal;

wherein the signals from each of the fixed elements are compared to each other.

13. The positioning system of claim 12 wherein the fixed element is a fixed resistor.

14. The positioning system of claim 9, wherein the sensors are equidistant on circuit legs and centered around the axis.

15. The positioning system of claim 14, further comprising a voltage source to provide a specified voltage to each circuit leg.

16. The positioning system of claim 9 wherein the fixed element has a fixed resistive value corresponding to and a value of the variable element on a circuit leg.

* * * * *